: 
United States Patent
Elsenhans et al.

(10) Patent No.: US 6,882,425 B1
(45) Date of Patent: Apr. 19, 2005

(54) METHOD AND APPARATUS FOR EXAMINING FLUIDS OF BIOLOGICAL ORIGIN

(75) Inventors: Olivier Elsenhans, Sins (CH); Emad Sarofim, Hagendorn (CH); Urban Georg Schnell, Muntschemier (CH)

(73) Assignee: Roche Diagnostics Corporation, Indianapolis, IN (US)

( * ) Notice: Subject to any disclaimer, the term of this patent is extended or adjusted under 35 U.S.C. 154(b) by 126 days.

(21) Appl. No.: 10/018,080

(22) PCT Filed: Jun. 7, 2000

(86) PCT No.: PCT/EP00/05237

§ 371 (c)(1),
(2), (4) Date: Dec. 10, 2001

(87) PCT Pub. No.: WO00/77494

PCT Pub. Date: Dec. 21, 2000

(30) Foreign Application Priority Data

Jun. 11, 1999 (EP) .............................. 99810517

(51) Int. Cl.$^7$ ............................... G01N 21/00
(52) U.S. Cl. ................. 356/436; 356/432; 356/40
(58) Field of Search ............... 356/432–436, 356/441, 408–410, 39–42; 364/498; 436/8, 50, 52, 60; 250/301, 339.6, 339.12

(56) References Cited

U.S. PATENT DOCUMENTS

| 4,267,572 A | * | 5/1981 | Witte ........................... 702/23 |
| 4,677,079 A | * | 6/1987 | Langhals ..................... 436/164 |
| 5,137,023 A | * | 8/1992 | Mendelson et al. .......... 600/316 |
| 5,424,840 A | * | 6/1995 | Moore et al. ................ 356/410 |
| 5,573,952 A | * | 11/1996 | Moessner ....................... 436/8 |

FOREIGN PATENT DOCUMENTS

| DE | 4433827 A1 | * | 3/1996 |
| EP | 0 562 800 A | | 9/1993 |
| EP | 0 915 338 A | | 5/1999 |
| US | 4263512 | | 4/1981 |
| WO | WO 91 04470 | | 4/1991 |
| WO | WO 97/19340 | | 5/1997 |

* cited by examiner

Primary Examiner—Richard A. Rosenberger
Assistant Examiner—Sang H. Nguyen
(74) Attorney, Agent, or Firm—Brinks Hofer Gilson & Lione

(57) ABSTRACT

A quality test of fluids of biological origin can be performed optically with applying a suitable evaluation method. In case of two components to be determined in a such fluid, an extinction spectrum is approximated in a first wavelength range by a combination of a merely theoretical curve and the spectrum of the pure first substance in a first wavelength range, and this evaluation is repeated in a second wavelength range this time by approximating the measured spectrum (62) by a combination of a hypothetical curve, the spectrum (64) of the first component with the already determined concentration, and the spectrum (65) of the pure second component. Furthermore, it is feasible to subtract the first and second spectrum and analyze the so obtained differential spectrum (66) in view of anomalies. The hypothetical curves are preferably straight lines which are defined by slope and ordinate section. In the praxis of the quality test of blood, bilirubin and hemoglobin may be quantitatively be determined, whilst the background together with the lipid component can be qualitatively examined by means of the differential spectrum.

27 Claims, 9 Drawing Sheets

METHOD AND APPARATUS FOR EXAMINING FLUIDS OF BIOLOGICAL ORIGIN

This application is a nationalized application of PCT Application No. PCT/EP 00/05237, filed on Jun. 7, 2000, which claims priority to an European Patent Application No. 99810517.7, filed on Jun. 11, 1999. The disclosures of the priority applications are incorporated by reference herein in their entirety.

BACKGROUND

The present invention relates to a method for measuring the concentration of at least one component of a liquid biological sample before analysis of said sample by an in vitro diagnostic method, said component being apt to interfere with the measurement of a target analyte by means of said diagnostic method. It relates further to devices for executing the method.

Clinical laboratory tests are routinely performed on the serum or plasma of whole blood. The tests commonly employ a series of reactions which terminate after the generation of chromophores which facilitate detection by spectroscopic measurements. The accuracy of most spectroscopic tests is affected to some extent by in vitro interferences. In vitro interferences arise from the fact that biochemical analysis are performed in the complex matrices that make up biological fluids, e.g. serum, plasma or urine. These fluids contain numerous compounds that either have chemical groups that can react with the test reagents or can have the physical or spectral properties of the target analyte. Further, the chemical composition of body fluids can vary with the nature and the extent of disease processes. In vitro interferences can be classified into two classes: spectral and chemical interference. The most commonly observed interferences are hemolysis, icteria, and lipemia. Some 30% of samples obtained from clinic or hospitalized patients are hemolyzed, icteric, or lipemic. Main reasons for hemolysis are unskilled blood taking or sample preparation, for icteria the jaunice disease, and for lipemia fat nutrition before blood taking.

The goal of sample quality monitoring is the determination of the interfering substances hemoglobin, bilirubin, and lipid prior to conducting fully automated clinical laboratory tests in order to provide meaningful and accurate test results. If a sample is sufficiently contaminated with interference substances, the test may either not be conducted or the test result may be flagged to indicate that it is not reliable. Particularly, such a test is desirable in connection with the use of clinical-chemical analyzers which perform most of the analysis of a sample fully automatically and without taking into account any particular characteristics or properties of individual blood samples.

U.S. Pat. No. 4,263,512 describes a known method and device for semi-quantitative sample quality monitoring of hemoglobin and bilirubin using multiple wavelength measurements on diluted serum samples. This method has the following disadvantages:

- it does not provide a quantitative determination of any interfering substances contained in the sample, and
- it requires a special and specific conditioning of the sample. Alternative methods are chromatographic or clinical-chemical determination of the concentrations of interfering substances. The chromatographic measurement requires a long measurement time and delicate instrumentation, whereas the clinical-chemical determination is not suitable for reagentless measurement.

BRIEF SUMMARY

Therefore, it is an aim of the present invention to provide a method for estimating rapidly the concentration of at least one interfering component in a fluid biological sample to be analyzed by an in vitro diagnostic test.

The above aim is attained with a method according to the present invention. The invention also defines preferred embodiments and applications thereof and means for carrying out the method.

In a preferred method according to the invention, the combination or superposition of the extinction spectrum of this first one of the components in a pure state and a function approximating the background extinction is fitted to the measured spectrum of the fluid to be analyzed in a wavelength range, where the component to be determined shows a significant or characteristic shape of its extinction curve. The function approximating the background extinction may e.g. be a straight line, and in this case, the wavelength range is preferably chosen where the expected background extinction spectrum is similar to a straight line.

BRIEF DESCRIPTION OF THE DRAWINGS

The invention shall be further explained in referring to exemplary embodiments with reference to the Figure.

DETAILED DESCRIPTION OF THE DRAWINGS

A method according to the invention for sample quality monitoring of blood serum or plasma by optical absorption spectroscopy in the visible and near IR range is described hereinafter. The target measuring ranges are 0.1–10 g/l hemoglobin, 2–20 mg/dl (1 dl=0.1 liter) bilirubin and 100–2000 mg/dl lipid with a measurement accuracy of 20%.

Figure 1:
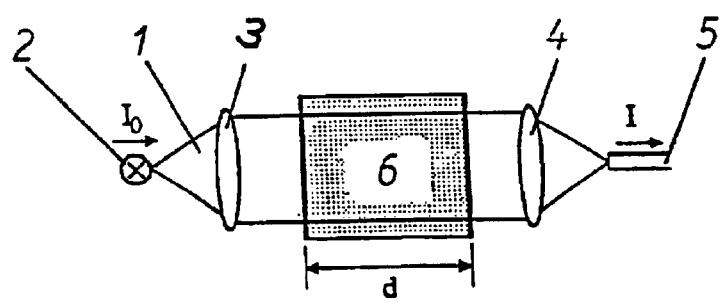
FIG. 1: Schematic representation of a photometric spectrum measurement arrangement.

The evaluation performed by the method according to the present invention yields e.g. the content of the hemoglobin and bilirubin. A quantitative determination of the lipid concentration by optical absorption spectroscopy is not possible due to a lack of a reproducible relation between light-scattering and lipid concentration. Therefore, a differential extinction spectrum is obtained by subtracting the hemoglobin and bilirubin contributions from the extinction spectrum of the target sample. It contains the spectral contributions of the lipid and the matrix, e.g. the blood serum or plasma, which can then be investigated for spectral anomalies. The method has been experimentally tested using a series of 125 synthetic test samples and a series of 92 real blood sera. Accuracy and reproducibility of the technique versus the performance of the spectroscopic measurement device are described and commented hereinafter. A basic setup for optical absorption spectroscopy for sample quality monitoring is shown in FIG. 1. A light beam 1 emitted by a multiple optical wavelength light source 2 is collimated by a lens 3, which directs light of spectral intensity $I_o(\lambda)$ to a target sample 6. The optical path within the target sample is denoted by d. A lens 4 collects transmitted light of intensity $I(\lambda)$, which is then detected by a spectral wavelength analyzer which has an input 5.

Optical absorption is commonly characterized by the extinction $E(\lambda)$, which is defined as $$\frac{I(\lambda)}{I_0(\lambda)} = 10^{-g(\lambda)}. \implies \log\frac{I(\lambda)}{I_0(\lambda)} = E(\lambda) \quad (1)$$

Figure 2:
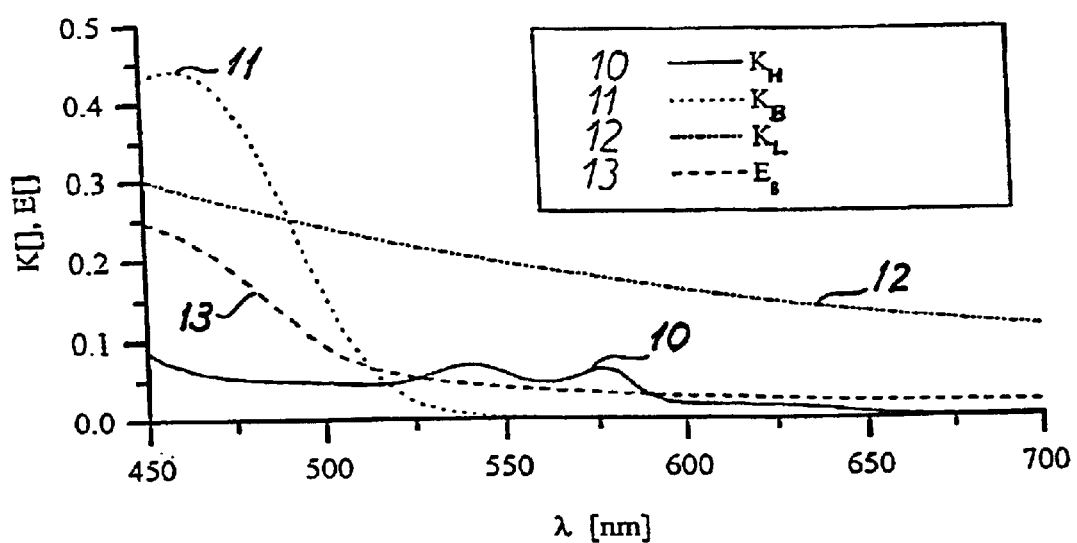
FIG. 2: Extinction spectra of pure interfering substances and a standard blood serum.

In the presence of J interfering substances in the target sample, e.g. hemoglobin, bilirubin and lipid (i.e., J=3), the extinction $E(\lambda)$ of the target sample can be described by the linear combination $$E(\lambda) = \sum_{j=1}^{J} K_j(\lambda)\frac{d}{q_{dil}}C_j + E_g(\lambda) \quad (2)$$

where $K_j$ and $C_j$ are the specific extinction coefficient and the concentration of interfering substance j (j=1, 2, ..., J), respectively. The dilution of the target sample is denoted by $q_{dil}$, i.e. (original concentrations): (sample concentrations)= $(1:q_{dil})$. $E_g$ is the extinction characteristic of the matrix, e.g. blood serum or plasma. In FIG. 2 the extinction coefficients $K_H$ of hemoglobin, $K_B$ of bilirubin, and $K_L$ of lipid (Intralipid 20% [Pharmacia, Sweden]) in the visible and near IR range are represented by lines 10, 11 and 12 respectively. The extinction spectrum $E_g$ of a standard blood serum (Control Serum N (human) [Hoffmann-La Roche, Switzerland]) is represented in FIG. 2 by dashed line 13.

Within the scope of sample quality monitoring, a minimum number $N_{min}$=4 of statistically independent extinction values $E(\lambda_n)$ (n=1, ..., 4) should allow the determination of the four unknown parameters in Eq. (2), i.e. the concentrations of the interference substances hemoglobin ($C_H$), bilirubin ($C_B$) and lipid ($C_L$), and the extinction component ($E_g$) corresponding to the matrix part. More reproducible results are expected by least squares fitting the mathematical model of the extinction spectrum defined by Equation (2) to $N>N_{min}$ measured values $E(\lambda_n)$ (n=1, 2, ..., N) in order to obtain best estimates of the values of $C_H$, $C_B$ and $C_L$.

However, it is observed that the specific extinction coefficient $K_L(\lambda)$ of lipid is not reproducible in real blood sera, and this is mainly due to the statistical distribution of the size of the scattering centers in the lipid. Moreover, as shown by FIG. 2, the monotonically decreasing extinction spectrum of lipid versus wavelength lacks typical (local) characteristics. Therefore, the latter spectrum cannot be distinguished from the component ($E_g$) of the extinction spectrum which corresponds to the matrix.

Figure 3:
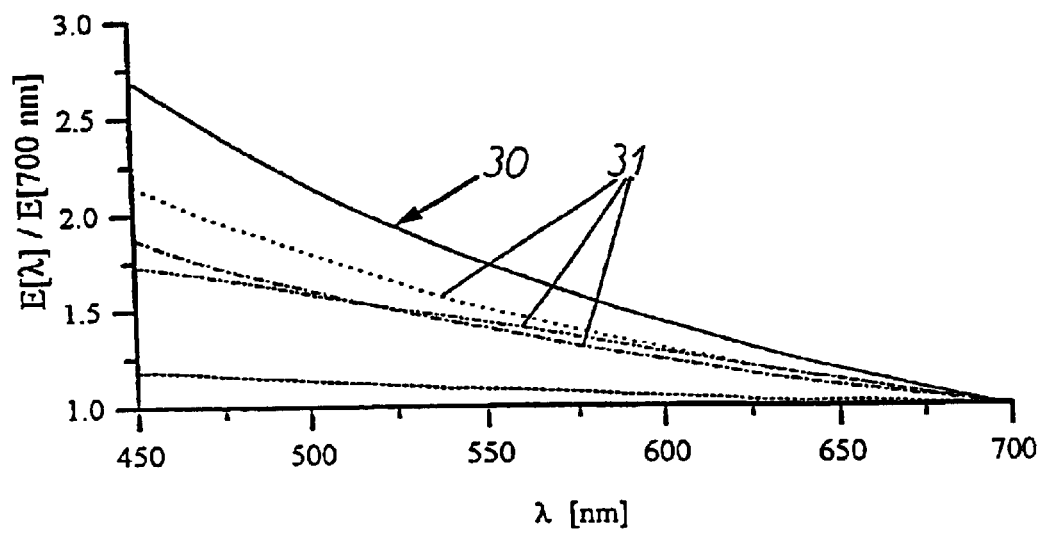
FIG. 3: Normalized extinction spectra of real whole blood sera, bilirubin and hemoglobin contribution being subtracted, and a reference lipid solution sample.

FIG. 3 shows extinction spectra 31 of real whole blood sera, from which the hemoglobin and bilirubin contributions have been subtracted. These differential spectra 31 therefore represent the sum of the spectral contributions of the lipid and the matrix. The shown extinction spectra are normalized to the extinction at $\lambda$=700 nm. The solid line 30 represents the extinction spectrum of the reference solution of Intralipid, the broken lines 31 represent the extinction spectra of several samples of real whole blood sera after subtraction of the extinction contributions of hemoglobin and bilirubin.

Hence quantitative determination of the concentrations of hemoglobin ($C_H$), bilirubin ($C_B$) and lipid ($C_L$) does not appear to be possible by measuring the optical extinction spectrum of the target sample and fitting the model in Equation (2) to the measured values $E(\lambda_n)$.

Therefore, according to the invention, a sequential determination of first the hemoglobin ($C_H$) and then the bilirubin ($C_B$) concentration is proposed in order to obtain a differential spectrum $E_{diff}$ by subtracting the hemoglobin and bilirubin contributions from the measured extinction spectrum $E(\lambda)$. The differential spectrum $E_{diff}$ thus represents the sum of the contributions of the lipid ($E_L$) and the matrix ($E_g$) to the extinction spectrum $E(\lambda)$ of the target sample, and may additionally be investigated for spectral anomalies over the whole spectral range.

Figure 4:
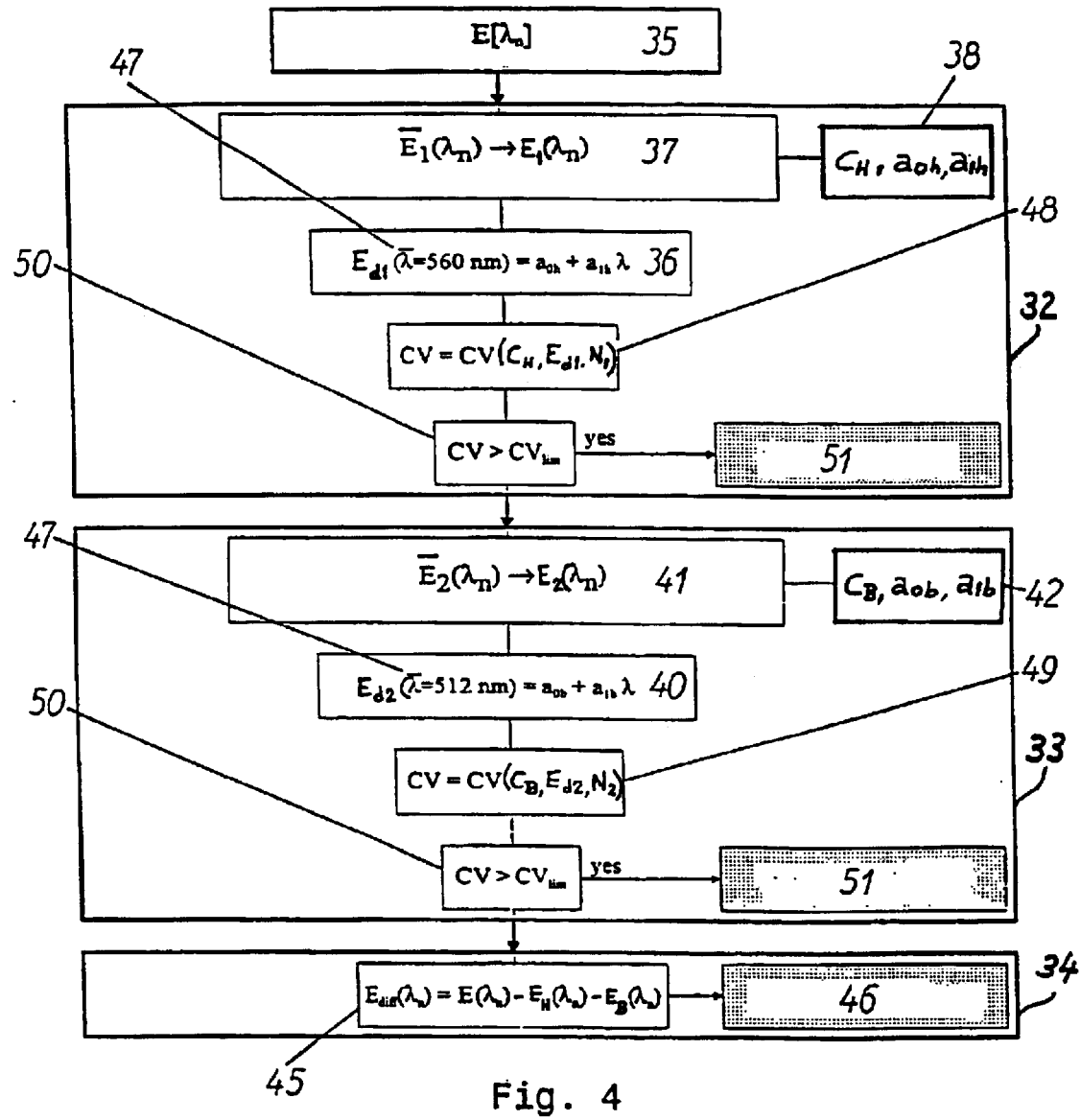
FIG. 4: Evaluation method for sample quality monitoring.

The bloc diagram in FIG. 4 summarizes an example of a proposed measurement and evaluation method according to the invention for sample quality monitoring.

This method is based on approximating the differential spectrum $E_{diff}=E_g+E_L$ in a limited wavelength range $\lambda_r$ by a straight line.

In a first step 32, the hemoglobin concentration is determined from a first measured extinction spectrum $E_1(\lambda)$ in a wavelength range $\lambda_{rh}\equiv[545, 575]$ nanometer. A set of extinction values comprising those of spectrum $E_1(\lambda)$ is represented by block 35. As shown by FIG. 2, within the wavelength range $\lambda_{rh}\equiv[545, 575]$ nanometer hemoglobin has typical spectral characteristics and the bilirubin contribution to the extinction spectrum is quasi negligible (FIG. 2).

In a curve fitting step 37, the mathematical model of the extinction spectrum defined by Equations (3) and (4) hereinafter is fitted by a linear least squares algorithm to $N_1$ spectroscopically measured values $E_1(\lambda_n)$ (n=1, 2, ..., $N_1$) in the range $\lambda_{rh}$.

In curve fitting step 37, the extinction spectrum $E_1(\lambda_n)$ is approximated by $$\overline{E}_1(\lambda) = E_{d1}(\lambda) + E_H(\lambda) \quad (3)$$

where $E_H(\lambda)$ is the hemoglobin contribution and is defined by $$E_H(\lambda) = K_H(\lambda)\frac{d}{q_{dil}}C_H \quad (4)$$

and $E_{d1}$ linearly approximates the sum of the lipid and the matrix contributions, and $E_{d1}$ is a function defined by $E_{d1} = a_{0h} + a_{1h}\lambda$. Note that the parameters $a_{0h}$ and $a_{1h}$ have no physical significance.

Fitting step 37 delivers the best estimate of the values of the hemoglobin concentration $C_H$ and $a_{0h}$, $a_{1h}$. This set of values is represented by block 38.

In a second step 33, the bilirubin concentration is determined from a second measured extinction spectrum $E_2(\lambda_n)$ in the wavelength range $\lambda_{rb} \cong [480, 545]$ nanometer. A set of extinction values comprising those of spectrum $E_2(\lambda)$ is also represented by block 35.

In a curve fitting step 41, the mathematical model of the extinction spectrum defined by Equations (5) and (6) hereinafter is fitted by a linear least squares algorithm to $N_2$ spectroscopically measured values $E_2(\lambda)$ ($n=1, 2, \ldots, N_2$) in the wavelength range $\lambda_{rb}$ In curve fitting step 41, the extinction spectrum $E_2(\lambda_n)$ is approximated by $$\overline{E}_2(\lambda) = E_H(\lambda) + E_{d2}(\lambda) + E_B(\lambda) \tag{5}$$

where $$E_B(\lambda) = K_B(\lambda) \frac{d}{q_{dil}} C_B \tag{6}$$

is the bilirubin contribution, $E_H$ is the previously determined hemoglobin contribution, and $E_{d2}$ linearly approximates the sum of the lipid and the matrix contributions and $E_{d2}$ is a function defined in particular by $E_{d2} = a_{0b} + a_{1b}\lambda$, and in general by $E_{dk}(\lambda, a_{i,Sk})$ with i ranging from 0 to at least 1. Note that the parameters $a_{0b}$ and $a_{1b}$ have no physical significance.

Fitting step 41 delivers the best estimate of the bilirubin concentration $C_B$ and $a_{0b}$, $a_{1b}$. This set of values is represented by block 42.

In a further method step 34, using Equations (2), (4) and (6), the differential spectrum $E_{diff}$ is obtained by the equation $$E_{diff}(\lambda) = E(\lambda) - E_H(\lambda) - E_B(\lambda), \tag{7}$$

The set of values of $E_{diff}$ is represented by block 45. This set of values can then be investigated for spectral anomalies and lead to results represented by block 46 which can be in particular indicative of an anomalous lipid content of the target sample.

The method according to the invention can be used to determine the concentration of k pure substances contained in a target sample.

For that purpose, in more general terms the method according to the invention comprises:

(a) measuring a first extinction spectrum $E_1(\lambda)$ of a liquid sample in a first selected wavelength range $\lambda = \lambda_{1,1}$ to $\lambda_{1,n}$, and (b) fitting an approximated spectrum $\overline{E}_1(\lambda)$ to said first measured extinction spectrum $E_1(\lambda)$, said approximated spectrum $\overline{E}_1(\lambda)$ being a combination of
a predetermined approximation function $E_{d1}(\lambda, a_{i,S1})$ for the background extinction, with i ranging from zero to at least one, and
a predetermined extinction spectrum $E_{S1}(C_{S1}, \lambda)$ of a first pure component of concentration $C_{S1}$ of the components to be determined,
said fitting being performed by varying said concentration $C_{s1}$ of said first interfering component and at least two of said coefficients $a_{i,S1}$, so that the deviation between said first measured extinction spectrum $E_1(\lambda)$ and said approximated spectrum $\overline{E}_1(\lambda)$ is minimized in order to determine the concentration of said first interfering component, and said first selected wavelength range being so selected that the concentration $C_{S1}$ of said first interfering component can be determined unambiguously.

In a preferred embodiment the approximated spectrum $\overline{E}_1(\lambda)$ is the sum of said predetermined approximation function $E_{d1}(\lambda, a_{i,S1})$ for the background extinction, and said predetermined extinction spectrum $E_{S1}(C_{S1}, \lambda)$ of said pure first component of concentration $C_{S1}$.

In order to determine the concentration of a k pure component of a target sample a method according to the invention further comprises (a) measuring at least one further extinction spectrum $E_k(\lambda)$ of said liquid sample in at least one further selected wavelength range $\lambda = \lambda_{k,1}$ to $\lambda_{k,n}$, with $k \geq 2$, and (b) fitting at least one further approximated spectrum $\overline{E}_k(\lambda)$ to said at least one further measured extinction spectrum $E_k(\lambda)$, said at least one further approximated spectrum $\overline{E}_k(\lambda)$ being a combination of
a predetermined approximation function $E_{dk}(\lambda, a_{i,Sk})$ for the background extinction, with i ranging from zero to at least one,
previously determined extinction spectrums $E_{SL}$ ($C_{SL}, \lambda$), with L varying from L=1 to k−1, of k−1 pure components previously determined, and
a predetermined extinction spectrum $E_{Sk}(C_{Sk}, \lambda)$ of a k pure component of concentration $C_{Sk}$ to be determined, said fitting being performed by varying the concentration $C_{Sk}$ and at least two of the coefficients $a_{i,Sk}$ so that the deviation between measured spectrum and approximated spectrum is minimized, in order to determine the concentration of the second component, said at least one further selected wavelength range being so selected that the concentration $C_{Sk}$ of said k pure component can be determined unambiguously.

In a preferred embodiment the approximated spectrum $\overline{E}_k(\lambda)$ is the sum of said predetermined approximation function $E_{dk}(\lambda, a_{i,Sk})$ for the background extinction, said previously determined extinction spectrums $E_{SL}$ ($C_{SL}, \lambda$), with L varying from L=1 to k−1, of k−1 pure components previously determined, and said predetermined extinction spectrum $E_{Sk}(C_{Sk}, \lambda)$ of said k pure component of concentration $C_{Sk}$.

Reproducibility

The reproducibility of the measured concentration $C_H$ of hemoglobin and of the measured concentration $C_B$ of bilirubin can be analytically calculated, if the minimum number $N_{min}=3$ of measured extinction values $E(\lambda_n)$ in the range $\lambda_{rh}$ are used to determine $C_H$ from Equation (3) by means of the above described fitting step 37, and if the minimum number $N_{min}=3$ of measured extinction values $E(\lambda_n)$ in the range $\lambda_{rb}$ are used to determine $C_B$ from Equation (5) by means of the above described fitting step 41.

The reproducibility of a measured concentration C is commonly characterized by the coefficient of variation $CV = \sigma_c / E\{c\}$, where $\sigma_x$ and $E\{x\}$ stand for the standard deviation and the statistical expectation (mean value) of $\{x\}$, respectively. Using Equations (1), (2), and (7), it can be readily shown that the coefficient of variation CV of the concentration $C_j$ is related to the reproducibility of the (physically) measured optical intensity $\sigma_I/I_0$ by the relation $$CV \big|_{N_{\min}} = \frac{\sigma_{C_j}}{E\{C_j\}} \equiv \frac{1}{D} \frac{\sigma_I}{I_0} \frac{1}{C_j} 10^{K_j(\overline{\lambda}) \frac{d}{q_{dil}} C_j + E_d(\overline{\lambda})}, \tag{8}$$

where $\overline{\lambda}$ is the center wavelength of the respective measurement range $\lambda_r$, $D = [\ln(10)/4] \cdot [2K_j(\lambda_2) - K_j(\lambda_1) - K_j(\lambda_3)] \cdot [d/q_{dil}]$, and $\ln(x)$ is the natural logarithm of (x).

In FIG. 4, the center wavelength $\bar{\lambda}$ at which $E_{d1}$ is calculated in method step 36 and $E_{d2}$ in method step 40, is pointed out by reference number 47.

Note that the background contribution $E_d(\lambda)$ of the lipid and the matrix significantly reduce the reproducibility of the measured concentration $C_j$.

When $N > N_{min}$ statistically independent measured values $E(\lambda_n)$ are used for the linear least squares algorithm, it can be shown that the coefficient of variation CV of the measured hemoglobin concentration, as well as the coefficient of variation CV of the measured bilirubin concentration, is related to Equation (8) by the relation $$CV|_N = \frac{1}{\sqrt{M}} CV|_{N_{min}}, \qquad (9)$$

where $M = N - N_{min}$ is the number of redundant measurements.

In FIG. 4, a method step 48 for computing the coefficient of variation CV of the measured hemoglobin concentration, and a method step 49 for computing the coefficient of variation CV of the measured hemoglobin concentration are represented.

From Equation (9) it can be appreciated that the reproducibility of the measured concentration increases with the number N of measured extinction values considered for the curve fitting method step. The number N is given by the spectral resolution and sampling rate of the spectroscopic measurement system and the wavelength range $\lambda_r$.

It should be noted that an extension of the wavelength range $\lambda_r$ increases N for a given spectral resolution and sampling rate, but that the linear approximation $E_d$ of the sum of the lipid and the matrix contributions in Equations (3) and (5) becomes more and more inaccurate. The value of the coefficient of variation CV, calculated from Equations (8) and (9), can then be compared in a comparison step 50 with a predetermined limit value $CV_{lim}$ in order to characterize the quality of the concentration measurement. If this comparison shows that a value of CV is larger than $CV_{lim}$ this provides an indication 51 of a critical to weak reproducibility of the results, that is of the concentrations and the differential spectrum. Consequently, the measurement would e.g. be disregarded, repeated, or marked as being of reduced reliability.

Sample quality monitoring, based on optical absorption spectroscopy as shown in FIG. 1, has been experimentally investigated using a state-of-the-art spectrometer (Cary V, VARIAN, Australia). The collimated beam had an approximate spot size of 5×2 square millimeter. The optical path in the test sample was d=10 mm. The sample dilution was 1:20 ($q_{dil}$=20). The spectrum of the test sample was measured in the wavelength range $\lambda$=[300, 1200] nanometer with a spectral resolution of $\Delta\lambda$=0.05 nanometer and a spectral sampling rate of $\Delta\lambda_s$=1 nanometer/pixel. The hemoglobin concentration $C_H$ has been obtained from linear least squares fitting the model in Equations (3) and (4) to $N_1$=28 measured values $E(\lambda_n)$ in the wavelength range $\lambda_{rh}$=[545, 575] nanometer. The bilirubin concentration $C_B$ has been obtained from linear least squares fitting the model in Equations (5) and (6) to $N_2$=63 measured values $E(\lambda_n)$ in the wavelength range $\lambda_{rb}$=[480, 545] nanometer. The differential extinction spectrum $E_{diff}$ has been obtained from Equation (7). The reproducibility of the measured hemoglobin and bilirubin concentrations has then been calculated according to Equations (8) and (9), with $\sigma_I/I_0 = 5 \cdot 10^{-5}$ for the reproducibility of the measured optical intensities.

Figure 5:
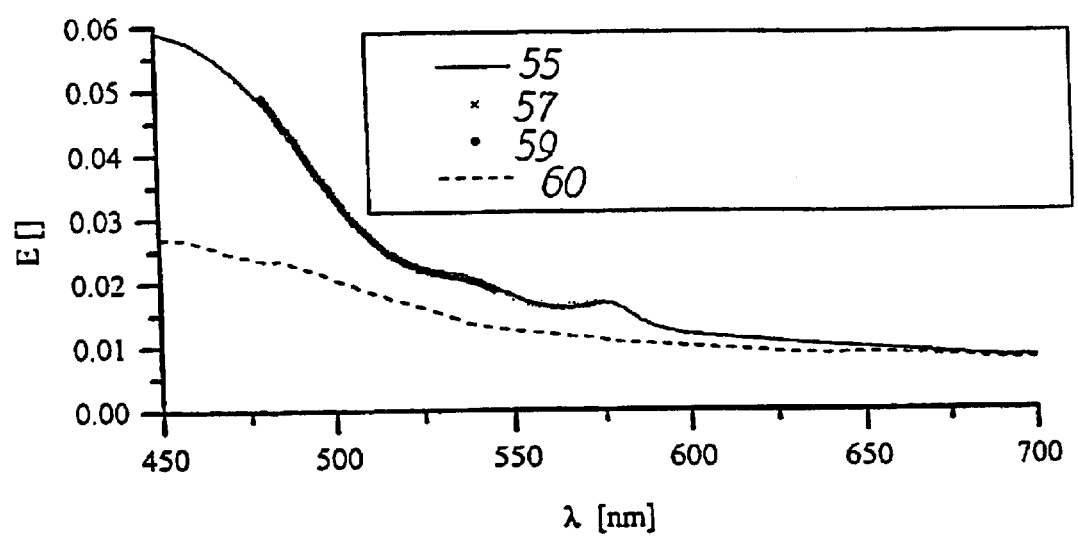
FIG. 5: Experimentally measured extinction spectrum of a real whole blood serum and results of the evaluation method.

As an example, FIG. 5 shows the experimentally measured extinction spectrum $E(\lambda)$ of a typical real whole blood serum 55. The best fitting extinction models for hemoglobin 57 and bilirubin 59 in Equations (3) and (5) are represented by crosses and dots, respectively. The best fitting hemoglobin and bilirubin concentrations are $C_H$=0.18 g/l (CV=1.5%) and $C_B$=0.67 mg/dl (CV=0.3%), respectively. The differential extinction spectrum $E_{diff}(\lambda_n)$ 60 is also shown by the dashed line.

Figure 6:
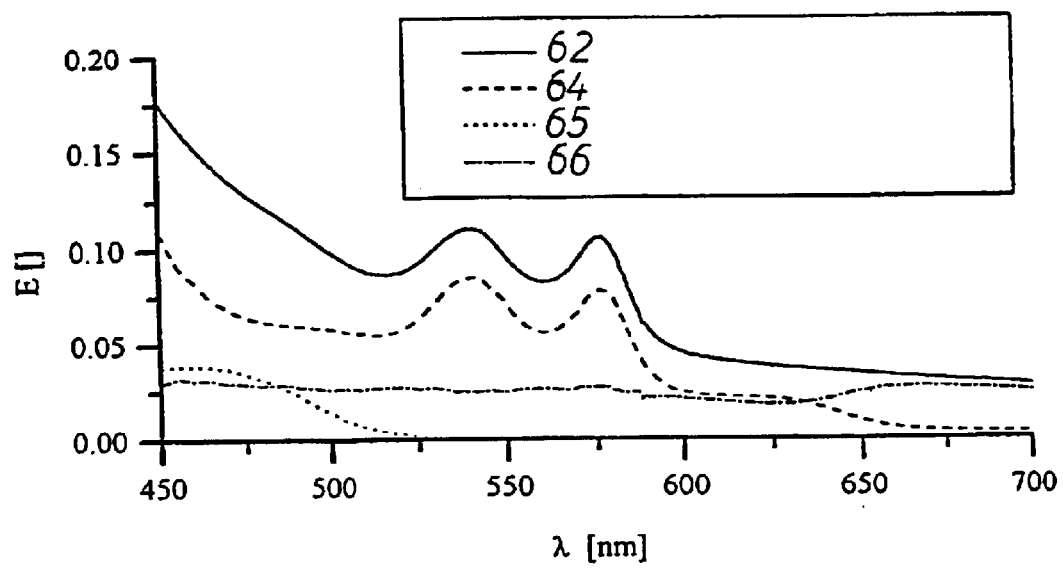
FIG. 6: Measured extinction spectrum of a strongly hemolytic whole blood sample and respective extinction spectra obtained by the examination method.
Figure 7:
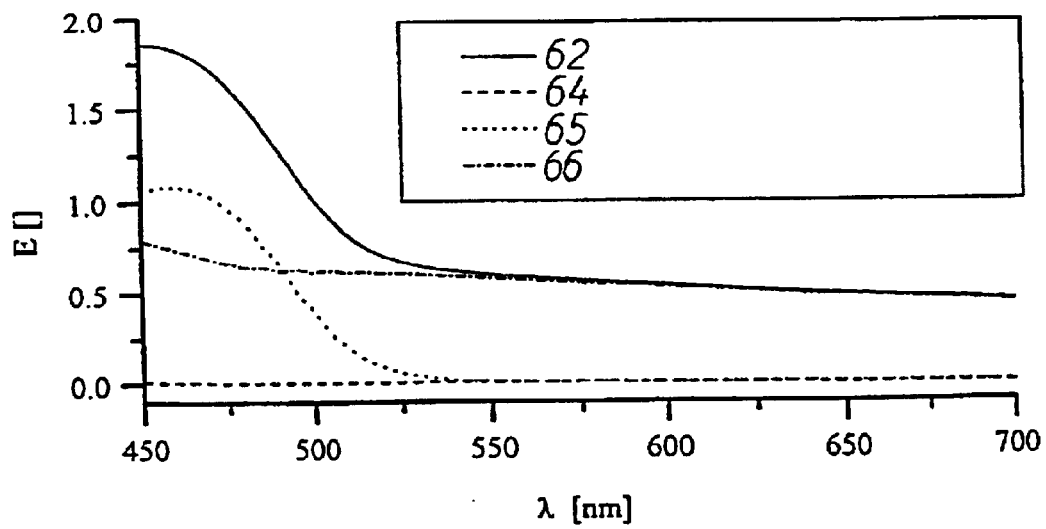
FIG. 7: As FIG. 6 for a strongly icteric whole blood sample.

FIGS. 6 and 7 show other examples of real whole blood serum samples, namely with a high hemoglobin content respectively an highly icteric sample. Furthermore, in FIG. 6, the differential spectrum shows an anomalous differential spectrum which is merely constant with additionally an increased extinction with increasing wavelength above about 650 nanometer. The continuous line 62 is the measured spectrum, the dashed line 64 and the dotted line 65 are the hemoglobin respectively the bilirubin contributions, and the dash-dotted line 66 is the differential spectrum, each time calculated from the results according to the described method.

Accuracy

Figure 8:
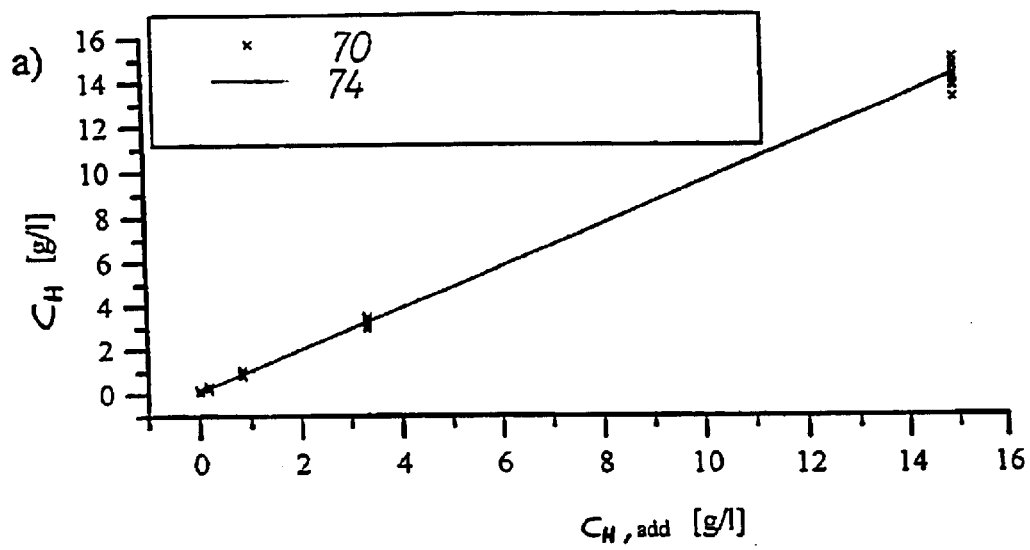
FIGS. 8, 9: Optically determined hemoglobin (FIG. 8) and bilirubin (FIG. 9) concentrations versus added concentrations for 125 independent test samples.
Figure 9:
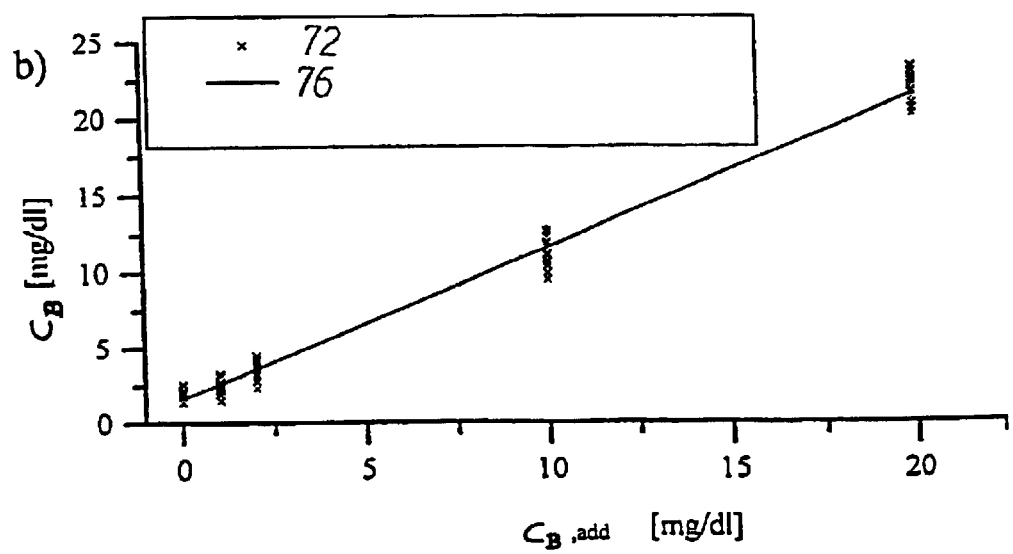

In order to investigate the accuracy of the method, the hemoglobin and bilirubin concentrations of a series of 125 independent test samples have been determined. The samples have been synthesized using a standard blood serum (Control Serum N (human) [Hoffmann-La Roche, Switzerland]) to which hemoglobin (Hemolysat [Hoffmann-La Roche, Switzerland]), bilirubin (B-4126 mixed isomers [Sigma, Switzerland]) and lipid (Intralipid 20% [Pharmacia, Sweden]) have been added. The added concentrations of hemoglobin, bilirubin and lipid were $C_H$=[0, 0.17, 0.83, 3.33, 15] g/l, $C_B$=[0, 1, 2, 10, 20] mg/dl and $C_L$=[0, 50, 100, 400, 1800] mg/dl, respectively, leading to the set of 5.5.5 test samples. The optically measured hemoglobin 70 and bilirubin 72 concentrations versus added concentrations are represented in FIGS. 8 and 9.

In the case of hemoglobin (FIG. 8), a linear least squares fit 74 ($C_{fit,h}=c_{0,h}+m_h C_H$) yields an offset concentration $c_{0,h}$= 0.12 g/l and a slope $m_h$=0.95. The correlation coefficient between the best fit and the measured values is $\rho$=0.999. In the case of bilirubin (FIG. 9), a second linear least squares fit 76 ($C_{fit,b}=c_{0,b}+m_b C_B$) yields an offset concentration $c_{0,b}$= 1.64 mg/dl and a slope $m_b$=0.999. The correlation coefficient between the best fit and the measured values is $\rho$=0.995. Note that Control Serum N (human) has an approximate bilirubin concentration of $C_B \cong 2$ mg/dl. Further, it is stated that the amount of added hemoglobin, bilirubin and lipid also has finite accuracy.

Figure 10:
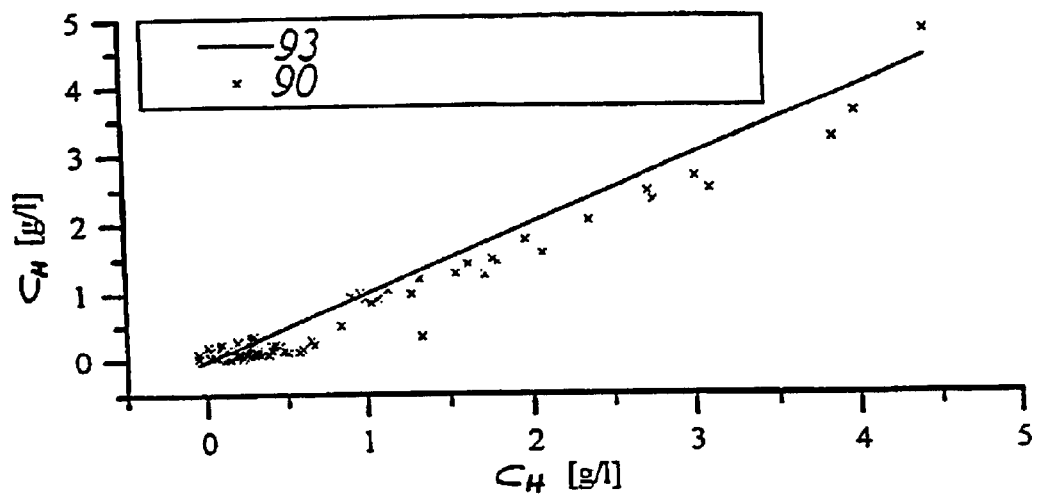
FIGS. 10,11: Optically measured hemoglobin respectively bilirubin concentration values vs. clinical-chemically measured concentration values for independent real whole blood sera.
Figure 11:
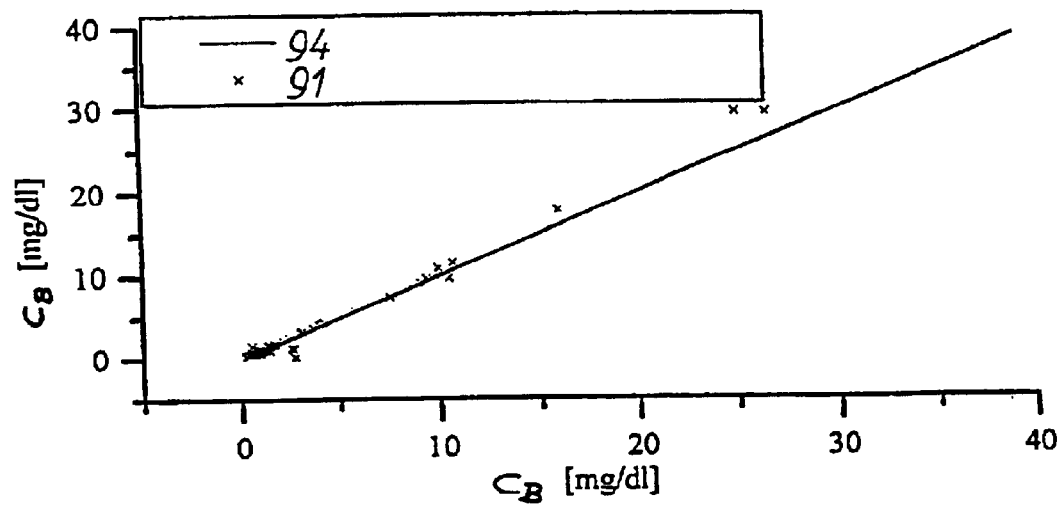
Figure 12:
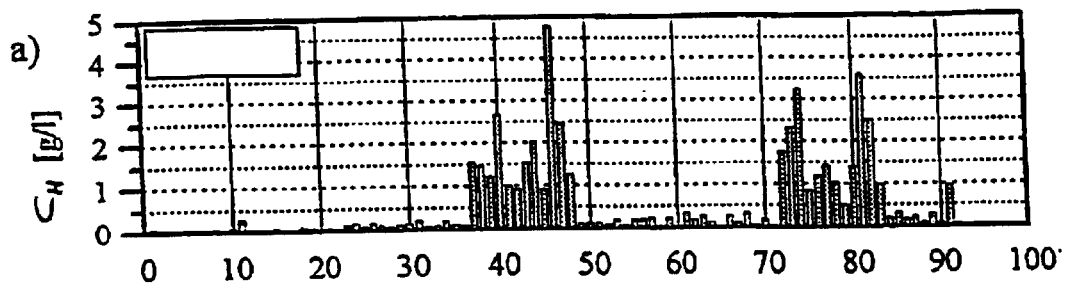
FIGS. 12–15: Optically measured hemoglobin and bilirubin concentrations of 92 real whole blood sera and the respective CV values obtained using a state-of-the-art spectrometer.

The hemoglobin and bilirubin concentrations of a series of 92 real whole blood sera have then been optically determined. The concentration values were in the range $C_H$=[0, 5] g/l for hemoglobin and $C_B$=[0, 45] mg/dl for bilirubin. As reference values, the concentrations have been determined by clinical-chemical analysis(Cobas® Integra 700 analyzer, [Hoffmann-La Roche, Switzerland]). FIGS. 10 and 11 show the optically versus clinical-chemically determined hemoglobin [bilirubin] concentrations 90 [91].

The results show that the sensitivity of the method is approximately $C_{H,min} \cong 0.5$ g/l hemoglobin and $C_{B,min} \cong 2$ mg/dl bilirubin. The observed correlation coefficients between the reference 93 [94] and the optically determined 90 [91] hemoglobin [bilirubin] concentrations were $\rho$=0.980 and $\rho$=0.996, respectively. Note that the clinical-chemical method has also limited accuracy; namely the bilirubin concentrations (FIG. 11) show better correlation than the hemoglobin concentrations (FIG. 10), although the accuracy of the optically measured bilirubin concentration is affected by the accuracy of the hemoglobin concentration determination (sequential determination of hemoglobin and bilirubin, see above).

In comparison, the benchmark Hitachi-Formula (U.S. Pat. No. 4,263,512) evaluation algorithm has been used to evaluate the optical absorption spectra. The observed correlation coefficients between the reference and the Hitachi-Formula determined concentration values were $\rho=0.879$ for hemoglobin and $\rho=0.992$ for bilirubin.

Reproducibility

Figure 13:
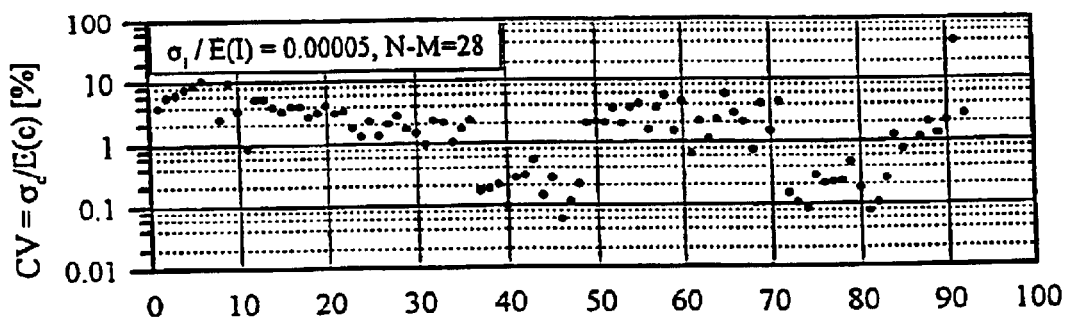
Figure 14:
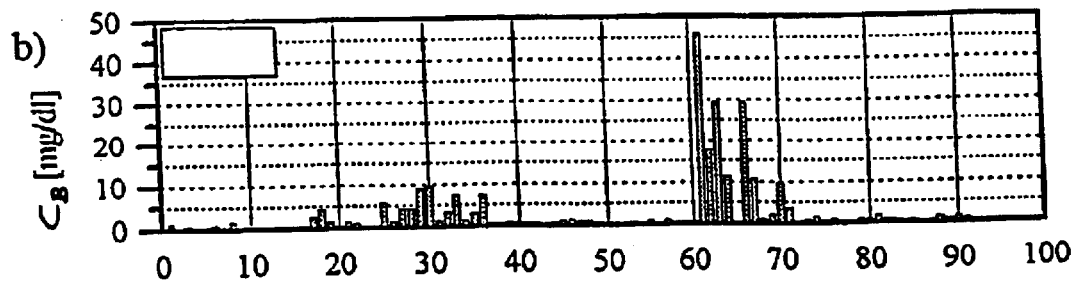
Figure 15:
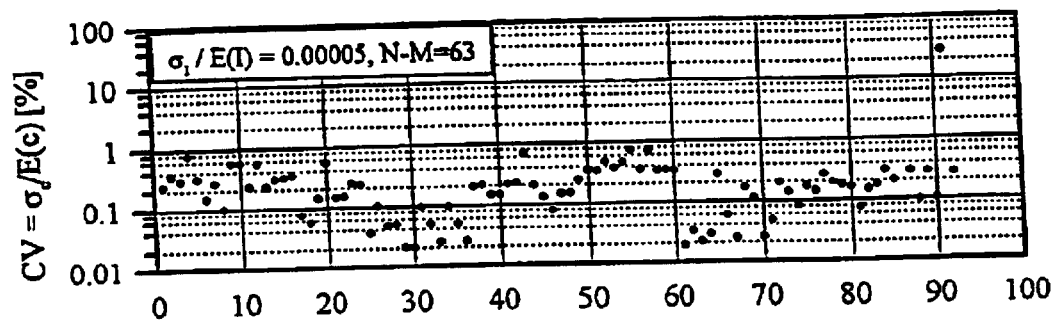

The coefficient of variation CV of the measured hemoglobin and bilirubin concentrations has been calculated from Equation (8), where $\sigma_I/I_0=5\cdot10^{-5}$ was the reproducibility of the measured optical intensities and $\bar{\lambda}=560$ nm was the center wavelength of $\lambda_{rh}$, for hemoglobin and $\bar{\lambda}=512$ nm for bilirubin was the center wavelength of $\lambda_b$. FIGS. 12 to 15 show the optically measured hemoglobin (FIG. 12) and bilirubin (FIG. 14) concentrations of the set of 92 real blood sera and the respective CV values (FIG. 13 respectively FIG. 15). Inspection of FIGS. 12 to 15 shows that the reproducibility is better for large concentration values, and that the values for hemoglobin and bilirubin are better than CV<10% respectively <1% for 89 respectively 91 of 92 analyzed sera.

Low Cost Optical Spectrometer Setup

Figure 16:
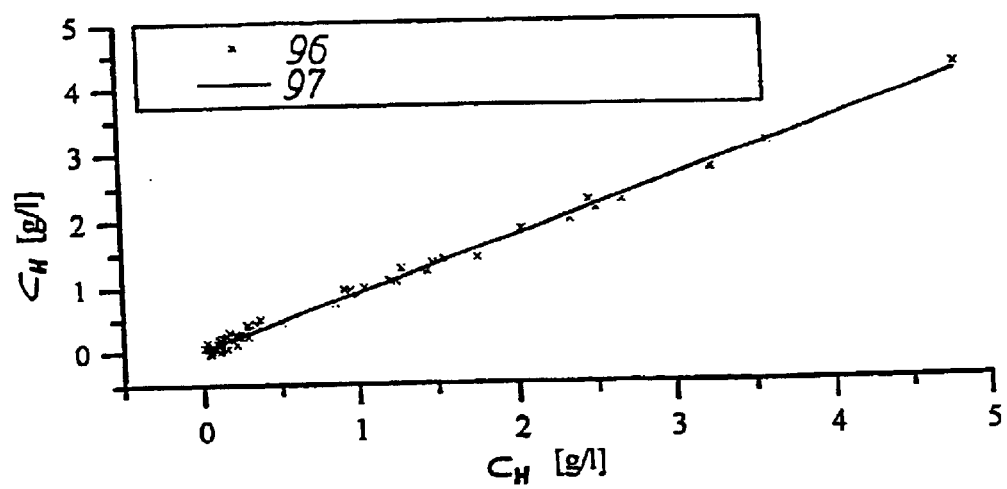
FIG. 16, 17: Low-cost versus state-of-the-art spectroscopically measured (FIG. 16) hemoglobin and bilirubin (FIG. 17) concentrations of 92 real whole blood sera.
Figure 17:
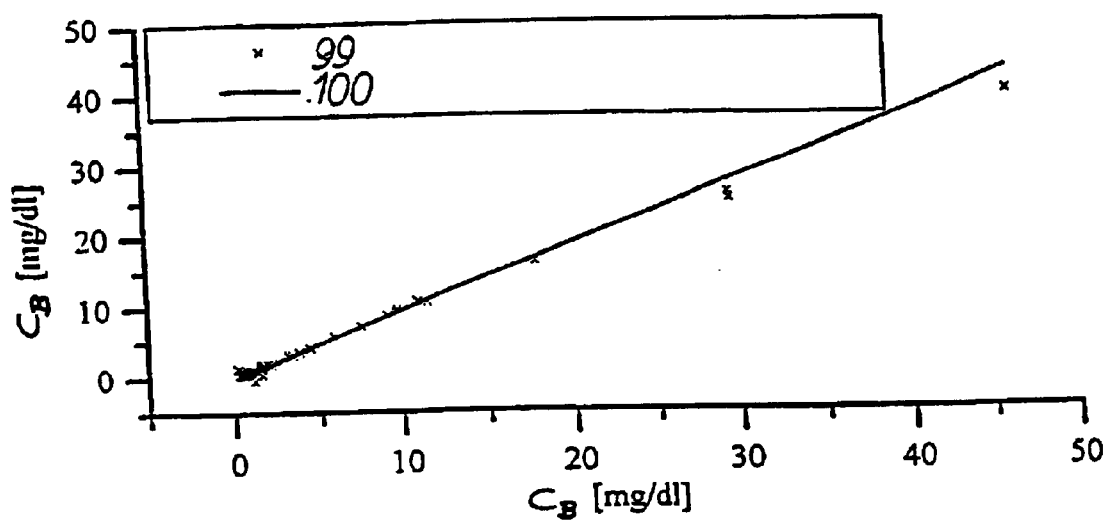

Sample quality monitoring, based on optical absorption spectroscopy as shown in FIG. 1, has then been experimentally investigated with low cost optical elements. The multiple optical wavelength light source was a white-light halogen lamp (Halogen 5V, 5W, $P_v\cong 2$ nW/nanometer @ $\lambda=530$ nanometer [MICROPARTS GmbH, Germany]). The collimated beam had an approximate diameter of D=2 mm. The optical path in the test sample was d=10 mm. The dilution of the sample was 1:20 ($q_{dil}=20$). The transmitted light was collected by a lens (focal length f=5 mm) and coupled into an optical fiber with core diameter $\varnothing_c=100\,\mu$m. The light was spectroscopically analyzed by a low cost, plane-concave spectrometer PCS [CSEM-Z, Switzerland] with spectral resolution $\Delta\lambda\cong 8$ nanometer. The spectrum of the test sample was measured by a linear photodiode array (512 pixels, center-to-center spacing $\lambda x=25\,\mu$m) in the wavelength range $\lambda=[421, 704]$ nanometer. The spectral sampling rate was $\Delta\lambda_s=2.8$ nanometer/pixel. The reproducibility of the measured optical intensities was $\sigma_I/I_0=5\cdot10^{-4}$. The hemoglobin concentration $C_H$ has been obtained from linear least squares fitting the model in Equations (3) and (4) to $N_1=11$ measured values $E(\lambda_n)$ in the wavelength range $\lambda_{rh}=[545, 575]$ nanometer. The bilirubin concentration $C_B$ has been obtained from linear least squares fitting the model in Equations (5) and (6) to $N_2=20$ measured values $E(\lambda_n)$ in the wavelength range $\lambda_{rb}=[480, 545]$ nanometer. The differential extinction spectrum $E_{diff}$ has been obtained from Equation (7). FIGS. 16 and 17 show the PCS versus the state-of-the-art (Cary V) spectroscopically measured hemoglobins 96 respectively bilirubin concentrations 99 of the set of 92 blood sera of FIGS. 10, 11 and 12 to 15. In the case of hemoglobin (FIG. 16), a linear least squares fit 97 ($c_{fit,h}=c_{0,h}+m_hC_H$) in the concentration range $C_H<2$ g/l yields an offset concentration $c_{0,h}=0.043$ g/l and a slope $m_h=0.859$. The correlation coefficient between the best fitting curve and the PCS measured values is $\rho=0.997$. In the case of bilirubin (FIG. 17), a linear least squares fit 100 ($c_{fit,b}=c_{0,b}+m_bC_B$) in the concentration range $C_B<15$ mg/dl yields an offset concentration $c_{0,b}=-0.010$ mg/dl and a slope $m_b=0.940$. The correlation coefficient between the best fitting curve and the PCS measured values is $\rho=0.998$. The results show that low cost spectrometers can readily be used for sample quality monitoring purposes.

If the examination of the samples yields a result indicating an anomalous condition of the sample, there may be generated by the examining device, e. g., one or more of the following signals or responses:

- an optical and/or acoustical warning signal to excite the operator's attention, particularly in case an abnormal sample has been detected,
- a printout of results (spectra, coefficients etc.) on a printer,
- a print on the analyzer's printout, so that the operator can immediately see if the results of the regular, chemical-clinical examination are true or prone to artefacts, or
- an automatic repetition of the measurement, e.g. using a new test sample.

Figure 18:
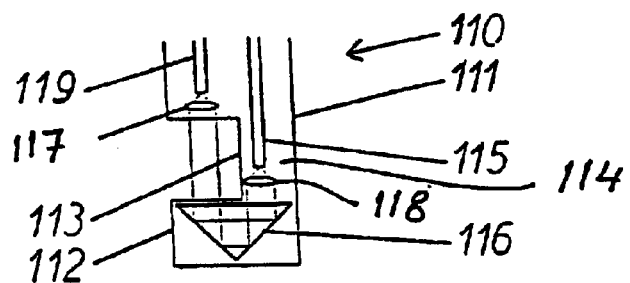
FIG. 18: Schematic illustration of a dip probe.

The described method may be implemented in various arrangements, preferably in connection with an automated analyzer, e g. as follows:

- The quality test may be done as a first photometric pass in the photometric site of an analyzer. Thereby, the performance of the analyzer is reduced because this prescan and the regular photometric pass are performed subsequently, or an additional sample is needed causing consumption of sample material;
- An additional photometric site is provided for the quality test;
- The pipette, or more generally, the supply system of the analyzer for the fluids to be tested, is provided with a transparent site, i.e. an optical flow-through cell (OFTC), in connection with a photometer; where necessary, particularly when the conduit system subsequently provides differently diluted samples, there may be arranged different OFTC paths with different optical path lengths in connection with flow switches for compensating the varying dilutions;
- A stand-alone photometer dedicated to the quality tests
- A dip-in probe 110 having e.g. a structure of the type shown by FIG. 18. Probe 110 has a tubular body 111 and is adapted to be immersed into a liquid sample contained in a sample container. Light guides 115 and 119 are arranged within and extend along the length axis of tubular body 111. Tubular body 111 has an end part 112 and a recess 113 spaced from end part 112. Tubular body has a segment 114 of reduced cross-section. The position of this segment corresponds to the position of recess 113. Lenses 117 and 118, and a prism 116 arranged within tubular body 111 at the end 112 thereof complete the structure of dip-in probe 110. Light transmitted through light guide 115 and lens 118 impinges on and is reflected back by prism 116, traverses recess 113, where a volume of the liquid sample to be examined is present, is collected by lens 117 and is transmitted to a photometer via light guide 119.
- The sample tube itself may be used as the photometric cuvette, provided the differing lengths of the optical observation paths can be compensated for, i. e. the path lengths are determined and can be input into the quality test system, and/or the sample tubes are of sufficiently equal size so that the optical paths do only differ within small limits, maybe in an even negligible variation range.

From the above description, variations of the invention are conceivable to the one skilled in the art without leaving the scope of the invention as defined in the claims. For instance, it is conceivable:

- to extend the method to the determination of a third and further components by continuing the sequential determination method using two, three, four etc. previously determined components for ascertaining the concentrations of a third, fourth etc. component;

to have the differential spectrum analyzed automatically by determining its curvature (i.e. the second derivative) and/or slope (i.e. the first derivative), which should increase respectively be negative for increasing wavelength in the exemplary quality test set forth above;

to choose deviating wavelength ranges for the photometric measurements, particularly if the quality test is used for determining other components of the samples provided that the spectra to be combined in order to approximate the measured spectrum show peculiarities in the given wavelength range so that the approximation parameters, before all the concentration of the sought component, are unambiguously derivable;

to determine the differential spectrum in a subrange of the wavelength range used for the determination of the single components, or possibly even a range extending beyond this range.

The attached figures shall be further explained by referring to the following reference numbers.

LIST OF REFERENCE NUMBERS 1 beam of light
2 light source (multiple wavelenght)
3 lens
4 lens
5 input of wavelength analyzer
10 extinction coefficient $K_H$ of hemoglobin
11 extinction coefficient $K_H$ of bilirubin
12 extinction coefficient $K_L$ of lipid
13 extinction coefficient $E_g$ of a standard blood serum
30 extinction spectra of the reference solution of Intralipid
31 extinction spectra of several samples of real whole blood sera
32 method step: determination of hemoglobin concentration
33 method step: determination of bilirubin concentration
34 method step: determination of $E_{diff}$ and further evaluation
35 measured extinction spectrum $E(\lambda)$ 35 in the approximate wavelength range $\lambda_{rh}$=[545, 575] nm
36 determination of $E_{d1}$ at $\bar{\lambda}$=560 nm
37 method step: curve fitting
38 set of values: $C_H$ and $a_{0h}$, $a_{1h}$
40 determination of $E_{d1}$ at $\bar{\lambda}$=512 nm
41 method step: curve fitting
42 set of values: $C_B$ and $a_{0b}$, $a_{1b}$
45 determination of $E_{diff}$
46 method step: investigation for spectral anomalies 46
47 center wavelength
48 computation of the coefficient of variation CV of the measured hemoglobin concentration
49 computation of the coefficient of variation CV of the measured bilirubin concentration
50 comparison step
51 indication of a critical to weak reproducibility of the results
55 measured extinction spectrum $E(\lambda)$ of a typical real whole blood serum
57 best fitting extinction model for hemoglobin
59 best fitting extinction models for bilirubin
60 differential extinction spectrum $E_{diff}(\lambda_n)$
62 measured spectrum
64 hemoglobin contribution
65 bilirubin contribution
66 differential spectrum
70 optically measured hemoglobin concentration
72 optically measured bilirubin concentration
74 linear least squares fit
76 linear least squares fit
90 optically determined hemoglobin concentrations
91 optically determined bilirubin concentrations
93 clinical-chemically determined hemoglobin concentrations
94 clinical-chemically determined bilirubin concentrations
96 state-of-the-art (Cary V) spectroscopically measured hemoglobin concentrations
97 linear least squares fit
99 state-of-the-art (Cary V) spectroscopically measured bilirubin concentrations
100 linear least squares fit
110 dip-in probe
111 tubular body
112 end part of tubular body 111
113 recess
114 segment having a reduced cross-section
115 light guide
116 prism
117 lens
118 lens
119 light guide Many variations of the invention will become apparent to those skilled in the art upon review of this specification. Therefore, the scope of the invention should not be determined with reference to the above description, but should be determined with reference to the appended claims along with their full scope and equivalents.

What is claimed is:

1. A method for measuring a concentration of hemoglobin and bilirubin in a sample of blood serum or blood plasma before analysis of said sample by an in vitro diagnostic method, in order to determine whether an amount of hemoglobin, bilirubin or lipid present in that sample can interfere with a measurement of a target analyte contained in said sample by means of said diagnostic method, said method for measuring comprising sequentially carrying out the following method steps:

(a) carrying out a first method step for determining the concentration of hemoglobin in said sample, said first method step including:

i) measuring a first extinction spectrum $E_1(\lambda)$ of said sample in a first selected wavelength range $\lambda_{rh}=\lambda_{1,1}$ to $\lambda_{1,n}$, the contribution of bilirubin to the extinction spectrum being much smaller than the contribution of hemoglobin within the first selected wavelength range, and ii) fitting a first approximated spectrum $\overline{E}_1(\lambda)$ to said first measured extinction spectrum $E_1(\lambda)$, said first approximated spectrum $\overline{E}_1(\lambda)$ being a combination of:

a predetermined first approximation function $E_{d1}(\lambda, a_{0h}, a_{1h})$ for a background extinction, with $a_{0h}$, $a_{1h}$ being coefficients, and a predetermined extinction spectrum $E_H(C_H, \lambda)$ of pure hemoglobin having a concentration $C_H$ to be determined, said fitting of said first approximated spectrum $\overline{E}_1(\lambda)$ to said first measured extinction spectrum $E_1(\lambda)$ being performed by varying said concentration $C_H$ of hemoglobin and said coefficients $a_{0h}$, $a_{1h}$, so that a deviation between said first measured extinction spectrum $E_1(\lambda)$ and said first approximated spectrum $\overline{E}_1(\lambda)$ is minimized in order to determine the concentration $C_H$ of hemoglobin, and (b) carrying out a second method step for determining the concentration of bilirubin in said sample, said second method step including:
   i) measuring a second extinction spectrum $E_2(\lambda)$ of said sample in a second selected wavelength range $\lambda_{rb} = \lambda_{2,1}$ to $\lambda_{2,n}$,
   ii) fitting a second approximated spectrum $\overline{E}_2(\lambda)$ to said second measured extinction spectrum $E_2(\lambda)$, said second approximated spectrum $\overline{E}_2(\lambda)$ being a combination of:
      a predetermined second approximation function $E_{d2}(\lambda, a_{0b}, a_{1b})$ for a background extinction, with $a_{0b}$, $a_{1b}$ being coefficients,
      a predetermined extinction spectrum $E_H(C_H, \lambda)$ of hemoglobin having a concentration $C_H$ determined in said first method step, and
      a predetermined extinction spectrum $E_B(C_B, \lambda)$ of pure bilirubin having a concentration $C_B$ to be determined,
      said fitting of said second approximated spectrum $\overline{E}_1(\lambda)$ to said second measured extinction spectrum $E_1(\lambda)$ being performed by varying said concentration $C_B$ of bilirubin and said coefficients $a_{0b}$, $a_{1b}$, so that a deviation between said second measured extinction spectrum $E_2(\lambda)$ and said second approximated spectrum $\overline{E}_2(\lambda)$ is minimized in order to determine the concentration $C_B$ of bilirubin.

2. The method of claim 1 wherein:
said first approximated spectrum $\overline{E}_1(\lambda)$ is the sum of said predetermined first approximation function $E_{d1}(\lambda, a_{0h}, a_{1h})$ for the background extinction, and said predetermined extinction spectrum $E_H(C_H, \lambda)$ of hemoglobin having a concentration $C_H$ to be determined; and
said second approximated spectrum $\overline{E2}(\lambda)$ is the sum of said predetermined second approximation function $E_{d2}(\lambda, a_{0b}, a_{1b})$ for the background extinction, said predetermined extinction spectrum $E_H(C_H, \lambda)$ of hemoglobin having a concentration $C_H$ and said predetermined extinction spectrum $E_B(C_B, \lambda)$ of bilirubin having a concentration $C_B$ to be determined.

3. The method of claim 1 wherein in order to determine whether the amount of lipid present in said sample can interfere with the measurement of the target analyte contained in said sample by means of said diagnostic method, said measuring method further comprises carrying a third method step for obtaining a differential spectrum $E_{diff}(\lambda)$ which is representative of the amount of lipid contained in said sample, said differential spectrum being defined by $$E_{diff}(\lambda)=E(\lambda)-E_H(\lambda)-E_B(\lambda)$$

wherein $E(\lambda)$ comprises said first measured extinction spectrum $E_1(\lambda)$ and said second measured extinction spectrum $E_2(\lambda)$,
wherein $E_H(\lambda)$ is the contribution of hemoglobin to the spectrum said contribution being obtained by said first method step, and
wherein $E_B(\lambda)$ is the contribution of bilirubin to the spectrum said contribution being obtained by said second method step.

4. The method of claim 3 wherein said differential spectrum $E_{diff}(\lambda)$ is computed over a wavelength range covering at least 30% of the whole wavelength range defined by the broadest combination of said first wavelength range defined by $\lambda_{1,1}$ and $\lambda_{1,n}$, and said second wave length range defined by $\lambda_{2,1}$ and $\lambda_{2,n}$, and the differential spectrum is subjected to an analysis in view of anomalies.

5. The method of claim 4 wherein the curvature or the slope of the differential spectrum $E_{diff}(\lambda)$ in at least one predetermined wavelength range is determined, the result compared with the expected value, and wherein the differential spectrum is estimated to be normal if the value compared have identical sign.

6. The method of claim 4 wherein the curvature and the slope of the differential spectrum $E_{diff}(\lambda)$ in at least one predetermined wavelength range is determined, the results compared with the expected values, and wherein the differential spectrum is estimated to be normal if the values compared have identical sign.

7. The method of claim 4 wherein the curvature or the slope of the differential spectrum $E_{diff}(\lambda)$ in at least one predetermined wavelength range is determined, the result compared with the expected value, and wherein the differential spectrum is estimated to be normal if the value compared have identical sign, with the magnitude resting in a predetermined range given by an upper and a lower limiting curve.

8. The method of claim 4 wherein the curvature and the slope of the differential spectrum $E_{diff}(\lambda)$ in at least one predetermined wavelength range is determined, the results compared with the expected values, and wherein the differential spectrum is estimated to be normal if the values compared have identical sign, with the magnitude resting in a predetermined range given by an upper and a lower limiting curve.

9. The method of claim 3 wherein said differential spectrum $E_{diff}(\lambda)$ is computed over a wavelength range covering at least 50% of the whole wavelength range defined by the broadest combination of said first wavelength range defined by $\lambda_{1,1}$ and $\lambda_{1,n}$, and said second wave length range defined by $\lambda_{2,1}$ and $\lambda_{2,n}$.

10. The method of claim 3 wherein said differential spectrum $E_{diff}(\lambda)$ is computed over a wavelength range covering about 100% or more of the whole wavelength range defined by the broadest combination of said first wavelength range defined by $\lambda_{1,1}$ and $\lambda_{1,n}$, and said second wave length range defined by $\lambda_{2,1}$ and $\lambda_{2,n}$.

11. The method of claim 3 wherein the first wavelength range is chosen in the range of about 500 to about 600 nanometer, and the second wavelength range is chosen in the range of about 400 to about 600 nanometer.

12. The method of claim 11 wherein said sample is estimated to be of critical condition if the differential spectrum is anomalous.

13. The method of claim 11 wherein the amount of lipid and the overall constitution of the sample are estimated to be normal if the differential spectrum has a negative slope or a positive curvature or both.

14. The method of claim 3 wherein the first wavelength range is chosen in the range of about 545 to about 575 nanometer, and the second wavelength range is chosen in the range of about 480 to about 545 nanometer.

15. The method of claim 3 wherein the first wavelength range is from about 545 to about 575 nanometer, and the second wavelength range is from about 480 to about 545 nanometer.

16. The method of claim 3, wherein the spectra are provided as electrical signals and furnished to an evaluation device comprising a processor which performs the method steps on the spectra under the control of a program, and wherein the results are stored in a storage means or presented to an operator.

17. The method of claim 16, wherein the storage means is a storage means for digital data.

18. The method of claim 17, wherein the data are presented to an operator by printing, displaying or audible sounds.

19. The method of claim 1 wherein said fitting of said approximated spectra to said measured values of extinction spectra is done by a last squares fitting method.

20. The method of claim 1 wherein said sample is marked as anomalous if the concentration of hemoglobin or the concentration of bilirubin or both are outside of a predetermined range.

21. The method of claim 1 wherein the first wavelength range is chosen in the range of about 500 to about 600 nanometer, and the second wavelength range is chosen in the range of about 400 to about 600 nanometer.

22. The method of claim 21 wherein said sample is estimated to be of critical condition if the concentration of hemoglobin or the concentration of bilirubin or both are outside of a predetermined range.

23. The method of claim 1 wherein the first wavelength range is chosen in the range of about 545 to about 575 nanometer, and the second wavelength range is chosen in the range of about 480 to about 545 nanometer.

24. The method of claim 1 wherein the first wavelength range is from about 545 to about 575 nanometer, and the second wavelength range is from about 480 to about 545 nanometer.

25. The method of claim 1, wherein the spectra are provided as electrical signals and furnished to an evaluation device comprising a processor which performs the method steps on the spectra under the control of a program, and wherein the results are stored in a storage means or presented to an operator.

26. The method of claim 25, wherein the storage means is a storage means for digital data.

27. The method of claim 26, wherein the data are presented to an operator by printing, displaying or audible sounds.

* * * * *